United States Patent [19]

Kehne et al.

[11] Patent Number: 4,734,120

[45] Date of Patent: Mar. 29, 1988

[54] DIPEPTIDES CONTAINING C-TERMINAL PHOSPHINOTHRICIN, A PROCESS FOR THEIR PREPARATION AND THEIR USE FOR CONTROLLING UNDESIRABLE PLANT GROWTH

[75] Inventors: Heinz Kehne, Hofheim am Taunus; Klaus Bauer, Rodgau; Hermann Bieringer, Eppstein/Taunus, all of Fed. Rep. of Germany

[73] Assignee: Hoechst Aktiengesellschaft, Frankfurt am Main, Fed. Rep. of Germany

[21] Appl. No.: 940,959

[22] Filed: Dec. 12, 1986

[30] Foreign Application Priority Data

Dec. 14, 1985 [DE] Fed. Rep. of Germany ...... 3544376

[51] Int. Cl.$^4$ .......................... A01N 57/26; C07F 9/02
[52] U.S. Cl. .............................................. 71/87; 71/86; 260/502.5 D; 260/502.5 G; 560/9; 560/22; 560/36; 560/39; 560/40; 560/41; 560/121; 560/123; 560/125; 560/147; 560/153; 560/156; 560/169; 560/124
[58] Field of Search ................. 260/502.4, 502.5 D, 260/502.5 G; 560/9, 22, 36, 39, 40, 41, 121, 123, 125, 147, 153, 156, 169, 124; 71/86, 87

[56] References Cited

U.S. PATENT DOCUMENTS

| | | | |
|---|---|---|---|
| 4,331,591 | 5/1982 | Baylis | 260/502.5 |
| 4,399,287 | 8/1983 | Baillie et al. | 260/502.4 |
| 4,469,643 | 9/1984 | Tsurvoka et al. | 260/502.4 |

FOREIGN PATENT DOCUMENTS

| | | | |
|---|---|---|---|
| 0085391 | 8/1983 | European Pat. Off. | 260/502.5 |
| 0127429 | 5/1984 | European Pat. Off. | 260/502.5 |
| 2717440 | 4/1977 | Fed. Rep. of Germany . | |
| 2848224 | 11/1978 | Fed. Rep. of Germany . | |
| 3312165 | 10/1984 | Fed. Rep. of Germany ... | 260/502.5 |
| 21191 | 12/1983 | Japan | 260/502.5 |
| 2031896 | 4/1980 | United Kingdom | 260/502.5 |

*Primary Examiner*—Michael L. Shippen
*Assistant Examiner*—Bruce D. Gray
*Attorney, Agent, or Firm*—Curtis, Morris & Safford

[57] ABSTRACT

Dipeptides containing C-terminal phosphinothricin of the formula

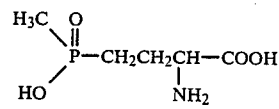

in which phosphinothricin is attached to a—preferably natural—amino acids at the amino group are effective herbicides in the pre-emergence and post-emergence techniques. The compounds are obtained, for example, by reacting phosphinothricin with the hydroxysuccinimide ester of an amino acids which is protected at the amino group in the presence of a base and subsequently splitting off the protective groups.

4 Claims, No Drawings

DIPEPTIDES CONTAINING C-TERMINAL PHOSPHINOTHRICIN, A PROCESS FOR THEIR PREPARATION AND THEIR USE FOR CONTROLLING UNDESIRABLE PLANT GROWTH

It is known that phosphinothricin (Ptc)

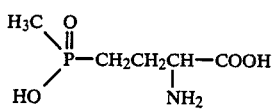

and certain peptides containing N-terminal Ptc display a good herbicidal activity (German Pat. No. 2,717,440; and German Pat. No. 2,848,224). It has now been found that peptides containing C-terminal Ptc also possess an excellent action as herbicides.

The invention therefore relates to dipeptides of the general formula I

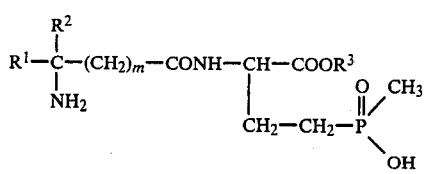

in which
R$^1$ and R$^2$ independently of one another denote hydrogen, (C$_1$-C$_{12}$)-alkyl, (C$_3$-C$_8$)-cycloalkyl, phenyl, benzyl or phenethyl, it being possible for the groups mentioned to be substituted in turn by halogen, NH$_2$, OH, SH, NO$_2$, (C$_1$-C$_4$)-alkoxy, (C$_1$-C$_4$)-alkylthio, CF$_3$, (C$_1$-C$_4$)-alkoxycarbonyl, COOH or CONH$_2$, or
R$^1$ and R$^2$ together denote an alkylene chain of 2-7 carbon atoms,
R$^3$ denotes hydrogen or (C$_1$-C$_{12}$)-alkyl and
m denotes 0, 1, 2 or 3,
and the salts thereof with bases and acids.

The compounds of the formula I contain 1 or 2 asymmetric carbon atoms. They can therefore exist in several stereoisomeric forms. The invention therefore relates not only to the racemates, but also to their stereoisomers and mixtures thereof in any desired proportions.

Preferred compounds are those in which
R$^1$ and R$^2$ independently of one another denote hydrogen, (C$_1$-C$_8$)-alkyl, phenyl, benzyl and phenylethyl, it being possible for the groups mentioned to be substituted in turn by NH$_2$, OH, SH, (C$_1$-C$_4$)-alkoxy, (C$_1$-C$_4$)-alkylthio, (C$_1$-C$_4$)-alkoxycarbonyl, COOH or CONH$_2$, or
R$^1$ and R$^2$, together with the carbon atom linking them, denote a cyclopentyl or cyclohexyl radical,
R$^3$ denotes hydrogen or methyl and m denotes 0, 1 or 2, and salts thereof.

Dipeptides which are particularly preferred are those of Ptc with "natural", i.e. proteinogenic amino acids, such as alanine (Ala), α-aminobutyric acid (Abu), asparagine (Asn), aspartic acid (Asp), cysteine (Cys), glutamine (Gln), glutamic acid (Glu), glycine (Gly), isoleucine (Ile), leucine (Leu), lysine (Lys), methionine (Met), ornithine (Orn), phenylalanine (Phe), serine (Ser), threonine (Thr), tyrosine (Tyr) and valine (Val).

Non-proteinogenic amino acids are also suitable as dipeptide components, for example phenylglycine (Phg) or norvaline (Nva).

Since the compounds of the formula I contain acid (—COOH or —P(O)OH) and basic (—NH$_2$) groups, they are capable of forming salts with bases and strong acids. Suitable salts with bases are, in particular, the alkali metal and alkaline earth metal salts (containing Na$^+$, K$^+$ or Ca$^{++}$), the ammonium salts and salts with organic ammonium bases, such as mono-, di- and tri-(C$_1$-C$_4$)-alkylammonium or mono-, di- and tri-hydroxyethylammonium salts, and also the benzylammonium, dibenzylammonium, phenylammonium, diphenylammonium and dicyclohexylammonium salts. Acids which are particularly suitable for forming salts at the amino group are strong acids, such as HCl, HBr, H$_2$SO$_4$, HNO$_3$, H$_3$PO$_4$, HClO$_4$ and benzenesulfonic acid.

The invention also relates to a process for the preparation of the compounds of the general formula I, which comprises
(a) reacting a compound of the formula II

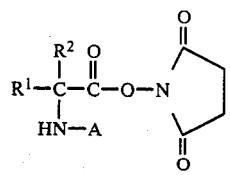

in which A denotes an amino protective group with phosphinothricin in the presence of an auxiliary base, or
(b) reacting a compound of the formula III

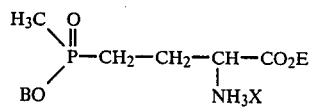

in which B and E are acid protective groups and X denotes the anion equivalent of a strong acid with a compound of the formula IV

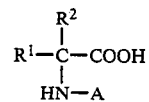

in the presence of an auxiliary base and a condensation agent,
and, if desired, subsequently splitting off the protective groups present in a known manner.

The N-acyl-amino acids (N-hydroxysuccinimide) esters of the formula II required for process variant (a) can be prepared by methods known from the literature (J. Am. Chem. Soc. 86, 1839 (1964), and Houben-Weyl Volume 15/2, page 149 et seq.). Because of their easy accessibility, the natural amino acids are particularly suitable as starting materials for their preparation. The protective groups A used are those customary in peptide chemistry, for example the carbobenzoxy (Cbo) group and the tert.-butoxycarbonyl (Boc) group. The reaction of II with phosphinothricin is preferably carried out in an aqueous organic solvent mixture, such as ethanol/water, 1,4-dioxane/water, tetrahydrofuran/water or 1,2-dimethoxyethane/water, or in a polar organic solvent, such as dimethylformamide, at temperatures between −20° C. and 60° C., preferably between −10° C. and 40° C. Suitable auxiliary bases in aqueous organic systems are, in particular, alkali metal hydroxides, such as sodium hydroxide, and in polar organic systems especially tertiary amines, such as triethylamine or N-ethylmorpholine.

The compounds of the formulae III and IV required for process variant (b) are obtained by methods which are generally known (German Offenlegungsschrift No. 2,717,440; Houben-Weyl Volume 15/1, page 315, Volume 12/1, page 247 et seq. and 423, and Volume 15/1, page 46 et seq.). Here too, the functional groups in the starting materials III and IV are protected by known methods of peptide chemistry; for example, lower alkyl and benzyl groups are suitable for protecting the acid groups in III. The attachment of the peptide bond is carried out in an inert organic solvent, such as $CH_2Cl_2$, tetrahydrofuran, 1,4-dioxane, acetonitrile, dimethylformamide, ethyl acetate or dimethoxyethane, at temperatures between −20° C. and 80° C., preferably between −10° C. and 50° C., in the presence of a condensation agent and an auxiliary base. The condensation agents used can be chloroformic acid esters, such as ethyl chloroformate, or dialkylcarbodiimides, such as dicyclohexylcarbodiimide. Suitable auxiliary bases are tertiary organic amines, such as triethylamine, N-ethylmorpholine or pyridine.

In process variants (a) and (b), protective groups remain in the molecule after the attachment of the peptide; these can be split off by methods known from the literature, for example the Cbo group by hydrogenolysis, the Boc group by acidolysis and ester groups by acid or alkaline hydrolysis.

Depending on the nature and sequence of the removal of the protective groups, the compounds I according to the invention are obtained in the free form or as salts. The salts can be converted into the free dipeptides by methods known from the literature (for example by reacting the hydrochlorides with propylene oxide). Salts are obtained from the free dipeptides by titration with one equivalent of acid or base and by evaporating the aqueous solution.

The compounds, according to the invention, of the formula I display an excellent herbicidal activity against a broad spectrum of monocotyledonous and dicotyledonous weeds of economic importance. Even perennial weeds which sprout from rhizomes, root-stocks or other long-lasting organs and are difficult to control are thoroughly dealt with by means of the active compounds. In this regard it is immaterial whether the substances are applied by the pre-sowing, pre-emergence or post-emergence technique.

The compounds of the formula I can be combined with numerous other herbicides; in some cases the mixtures possess a synergistic action. The following are examples of such mixing partners:

Triazines, such as 2-chloro-4-ethylamino-6-isopropylamino-1,3,5-triazine (atrazine), 2-chloro-4,6-bis-(ethylamino)-1,3,5-triazine (simazine), 2-tert.-butylamino-4-chloro-6-ethylamino-1,3,5-triazine (terbutylazine), 2-tert.-butylamino-4-ethylamino-6-methoxy-1,3,5-triazine (terbumeton), 2-ethylamino-4-isopropylamino-6-methylthio-1,3,5-triazine (ametryne), 2,4-bis(isopropylamino)-6-methylthio-1,3,5-triazine (prometryn) or 2-tert.-butylamino-4-ethylamino-6-methylthio-1,3,5-triazine (terbutryne), growth substances, such as 2,4-dichlorophenoxyacetic acid (2,4-D), 4-chloro-2-methylphenoxyacetic acid (MCPA), 4-chloro-2-methylphenoxypropionic acid (CMPP), 2-(2,4-dichlorophenoxy)-propionic acid (2,4-DP), 2,4,5-trichlorophenoxyacetic acid (2,4,5-T) or 3,6-dichloro-2-methoxybenzoic acid (dicamba) and esters and salts thereof, acetanilides, such as 2-chloro-2',6'-diethyl-N-methoxymethylacetanilide (alachlor), 2-chloro-6'-ethyl-N-(2-methoxy-1-methylethyl)-aceto-o-toluidide (metolachlor) or 2-chloro-N-(ethoxymethyl)-6'-ethylaceto-o-toluidide, phenylureas, such as 3-(3,4-dichlorophenyl)-1-methoxy-1-methylurea (linuron), 3-(3,4-dichlorophenyl)-1,1-dimethylurea (diuron), 3-(4-chlorophenyl)-1-methoxy-1-methylurea (monolinuron), and also methyl 2-[3-(4,6-dimethylpyrimidin-2-yl)-ureidosulfonyl]-benzoate, isopropylammonium 2-(4-isopropyl-4-methyl-5-oxo-2-imidazolin-2-yl)-nicotinate, 2-(4-isopropyl)-4-methyl-5-oxo-2-imidazolin-2-yl)-quinoline-3-carboxylic acid, methyl 2-[3-(4-chloro-6-methoxypyrimidin-2-yl)-ureidosulfonyl]-benzoate, 4-amino-6-tert.-butyl-4,5-dihydro-3-methylthio-1,2,4-triazin-5-one, 3-amino-1H-1,2,4-triazole, 2,6-dinitro-N,N-dipropyl-4-trifluoromethylaniline (trifluralin), ammonium ethylcarbamoylphosphonate and N-(phosphonomethyl)-glycine (glyphosate).

When the active compounds are applied to the green parts of plants by the post-emergence technique, a drastic cessation of growth sets in very rapidly after the treatment, and the weed plants remain in the state of growth existing at the time of application and wither more or less rapidly after a certain time, so that competition by weeds which is harmful to the crop plants can be eliminated in this manner very early and permanently by the use of the new agents according to the invention.

The compounds according to the invention also possess an excellent and very broad action against a wide spectrum of annual and perennial grass-like weeds and weeds which grow on road verges and in industrial or railroad works. The active compounds are therefore suitable both for use on areas not used for agriculture and for controlling weeds in agriculture. The use of non-selective compounds in annual or perennial agricultural crops is possible provided that it is ensured, through the nature of the application and/or the age of the crop plants, that the crop plants or their sensitive green parts do not get sprayed and thus suffer no damage. Examples of possible uses of this type are plantations, tree plantations, vineyards etc.

Since the use of the new compounds causes no damage to annual crops prior to the emergence of the crop plants or in the ripening stage of the latter, they can also be employed before sowing or shortly before or after harvesting with a view to minimum cultivation of the soil, control of late infestation by weeds and facilitating harvesting.

The invention also relates, therefore, to herbicidal agents containing the compound of the formula I and to the use thereof for controlling undesirable plant growth.

The agents according to the invention contain 2–95% of the active compounds according to the general formula I. Since the active compounds are in some cases soluble in water, they can advantageously be employed as aqueous solutions. In other cases, if they are not themselves water-soluble, they can be used in the customary preparation forms as emulsifiable concentrates, wettable powders and sprayable solutions.

Wettable powders are preparations which can be dispersed uniformly in water and which, in addition to the active compound and apart from a diluent or inert substance, also contain wetting agents, for example polyoxethylated alkylphenols, polyoxethylated oleylamines or stearylamines, alkylsulfonates or alkylphenylsulfonates, and dispersing agents, for example sodium ligninsulfonate, sodium 2,2'-dinaphthylmethane-6,6'-disulfonate, sodium dibutylnaphthalenesulfonate or sodium oleylmethyltauride.

Emulsifiable concentrates are obtained by dissolving the active compound in an organic solvent, for example butanol, cyclohexanone, xylene or higher-boiling aromatic compounds.

Wetting agents from the series mentioned above are also added in order to achieve good suspensions or emulsions in water.

In the case of herbicidal agents, the concentrations of the active compounds in the commercially available formulations can vary. In wettable powders, the active compound concentration varies, for example, between about 10% and 80%, the remainder being composed of the formulation additives indicated above. In the case of emulsifiable concentrates, the concentration of active compound is about 10% to 60%.

For use, the commercially available concentrates are optionally diluted in a customary manner, for example by means of water in the case of wettable powders and emulsifiable concentrates; sprayable solutions are not diluted further with other inert substances prior to use. The application are required varies with the external conditions such as temperature, humidity and others. It can vary within wide limits, for example between 0.1 kg/hectare and 10 kg/hectare of active substance, but is preferably between 0.3 and 3 kg/hectare.

The following examples serve to illustrate the invention further.

A. CHEMICAL EXAMPLES

Example 1: N-Dl-valyl-DL-phosphinothricin 36.2 g (0.2 mol) of DL-phosphinothricin are dissolved in 200 ml of 2N NaOH. 34.8 g (0.1 mol) of Cbo-DL-valinehydroxysuccinimide ester, dissolved in 60 ml of dioxane, are added dropwise at 0° C. The mixture is allowed to reach room temperature and dioxane (approx. 250 ml) is added until complete solution is achieved. After stirring for a further 15 hours at room temperature, the dioxane is removed in vacuo and the water phase is washed with ether and acidified to pH 1 with HCl. Extracting the water phase with ethyl acetate and drying the extract over $Na_2SO_4$ and evaporating it affords 39.2 g of crude N-Cbo-DL-valyl-DL-phosphinothricin.

The Cbo protective group is split off by dissolving the product in 200 ml of methanol, adding 4 g of 5% palladium-on-active charcoal and passing a stream of $H_2$ into the solution, warmed to 40° C., until no further evolution of $CO_2$ can be observed. The catalyst is filtered off and the solvent is removed in vacuo. This leaves 15.3 g (yield over both stages 55%) of N-DL-valyl-DL-phosphinothricin, melting point 128°–132° C. (decomposition).

Example 2: N-L-phenylalanyl-DL-phosphinothricin 13.2 g (0.036 mol) of DL-phosphinothricin dimethyl ester-hydrobenzenesulfonate and 10.8 g (0.036 mol) of Cbo-L-phenylalanine together with 3.6 g (0.036 mol) of triethylamine are dissolved in 100 ml of tetrahydrofuran. 10.3 g (0.05 mol) of dicyclohexylcarbodiimide (DCC), dissolved in 30 ml of THF, are added at 0° C., and the mixture is stirred for 24 hours at 0° C. Excess DCC is decomposed by means of 2 ml of glacial acetic acid, dicyclohexylurea is filtered off and the solvent is removed in vacuo. The residue is taken up in methylene chloride, and the organic phase is washed with 1N HCl, $NaHCO_3$ solution and water and is dried with $Na_2SO_4$ and concentrated. The residue is 17.5 g of crude N-Cbo-L-phenylalanyl-DL-phosphinothricin dimethyl ester, which is dissolved in 100 ml of methanol in order to split off the Cbo group. 3.5 g of concentrated HCl and 4 g of 5% palladium-on-active charcoal are added and $H_2$ is passed in at 40° C. until the evolution of $CO_2$ is complete. Filtering off the catalyst and evaporating the filtrate affords 12.4 g of crude N-L-phenylalanyl-DL-phosphinothricin dimethyl ester-hydrochloride, which is heated in 100 ml of concentrated HCl for 5 hours at 60° C. in order to saponify the ester groups. Evaporation and drying gives 7.7 g of crude N-L-phenylalanyl-DL-phosphinothricin hydrochloride, which is dissolved in 100 ml of absolute ethanol in order to liberate the free base. 10 ml of propylene oxide are added and the mixture is stirred for 10 hours at room temperature and the product is filtered off and dried. This gives 4.1 g (yield over all the stages 35%) of N-L-phenylalanyl-DL-phosphinothricin, melting point 121°–123° C. (decomposition).

The following compounds of the formula I listed in Table 1 can be obtained analogously.

TABLE 1*

| | H—Amino acid I—amino acid II—OH | | | |
|---|---|---|---|---|
| Example No. | Amino acid I | Amino acid II | | M.p. [°C.] |
| 3 | Gly | L-Ptc | | |
| 4 | Gly | DL-Ptc | | |
| 5 | Gly | DL-Ptc | HCl salt | |
| 6 | Gly | DL-Ptc | Na salt | |
| 7 | Gly | L-Ptc | HCl salt | |
| 8 | Gly | L-Ptc | Na salt | |
| 9 | L-Ala | L-Ptc | | |
| 10 | L-Ala | DL-Ptc | | 182 (decomp.) |
| 11 | DL-Ala | L-Ptc | | |
| 12 | DL-Ala | DL-Ptc | | |
| 13 | L-Ala | L-Ptc | HCl salt | |
| 14 | L-Ala | L-Ptc | Na salt | |
| 15 | L-Ala | DL-Ptc | HCl salt | |
| 16 | L-Ala | DL-Ptc | Na salt | |
| 17 | β-Ala | L-Ptc | | |
| 18 | β-Ala | DL-Ptc | | |
| 19 | L-Val | L-Ptc | | |
| 20 | L-Val | DL-Ptc | | |
| 21 | DL-Val | L-Ptc | | |
| 22 | DL-Val | DL-Ptc | | |
| 23 | L-Leu | L-Ptc | | |
| 24 | L-Leu | DL-Ptc | | 125–130 (decomp.) |
| 25 | DL-Leu | L-Ptc | | |
| 26 | DL-Leu | DL-Ptc | | |
| 27 | L-Ile | L-Ptc | | |
| 28 | L-Ile | DL-Ptc | | |
| 29 | DL-Ile | L-Ptc | | |
| 30 | DL-Ile | DL-Ptc | | |
| 31 | L-Phg | L-Ptc | | |
| 32 | L-Phg | DL-Ptc | | |
| 33 | DL-Phg | L-Ptc | | |
| 34 | DL-Phg | DL-Ptc | | 155 (decomp.) |
| 35 | D-Phe | DL-Ptc | | 135 (decomp.) |
| 36 | L-Phe | DL-Ptc | HCl salt | |
| 37 | DL-Phe | L-Ptc | | |
| 38 | DL-Phe | DL-Ptc | | 132-3 |

TABLE 1*-continued

H—Amino acid I—amino acid II—OH

| Example No. | Amino acid I | Amino acid II | | | M.p. [°C.] (decomp.) |
|---|---|---|---|---|---|
| 39 | L-Ser | L-Ptc | | | |
| 40 | L-Ser | DL-Ptc | | | |
| 41 | DL-Ser | L-Ptc | | | |
| 42 | DL-Ser | DL-Ptc | | | |
| 43 | L-Thr | L-Ptc | | | |
| 44 | L-Thr | DL-Ptc | | | |
| 45 | DL-Thr | L-Ptc | | | |
| 46 | DL-Thr | DL-Ptc | | | |
| 47 | L-Met | L-Ptc | | | |
| 48 | L-Met | DL-Ptc | | | |
| 49 | DL-Met | L-Ptc | | | |
| 50 | DL-Met | DL-Ptc | | | |
| 51 | L-Tyr | L-Ptc | | | |
| 52 | L-Tyr | DL-Ptc | | | |
| 53 | DL-Tyr | L-Ptc | | | |
| 54 | DL-Tyr | DL-Ptc | | | |
| 55 | L-Glu | L-Ptc | | | |
| 56 | L-Glu | DL-Ptc | | | |
| 57 | DL-Glu | L-Ptc | | | |
| 58 | DL-Glu | DL-Ptc | | | |
| 59 | L-Gln | L-Ptc | | | |
| 60 | L-Gln | DL-Ptc | | | |
| 61 | DL-Gln | L-Ptc | | | |
| 62 | DL-Gln | DL-Ptc | | | |
| 63 | L-Asp | L-Ptc | | | |
| 64 | L-Asp | DL-Ptc | | | |
| 65 | DL-Asp | L-Ptc | | | |
| 66 | DL-Asp | DL-Ptc | | | |
| 67 | L-Asn | L-Ptc | | | |
| 68 | L-Asn | DL-Ptc | | | |
| 69 | DL-Asn | L-Ptc | | | |
| 70 | DL-Asn | DL-Ptc | | | |
| 71 | L-Lys | L-Ptc | | | |
| 72 | L-Lys | DL-Ptc | HCl salt | glass | |
| 73 | DL-Lys | L-Ptc | | | |
| 74 | L-Lys | DL-Ptc | | | |
| 75 | L-Nle | L-Ptc | | | |
| 76 | L-Nle | DL-Ptc | | | |
| 77 | DL-Nle | L-Ptc | | | |
| 78 | DL-Nle | DL-Ptc | | | |
| 79 | L-Nva | L-Ptc | | | |
| 80 | L-Nva | DL-Ptc | | | |
| 81 | DL-Nva | L-Ptc | | | |
| 82 | DL-Nva | DL-Ptc | | | 155 (decomp.) |
| 83 | L-Cys | L-Ptc | | | |
| 84 | L-Cys | DL-Ptc | | | |
| 85 | DL-Cys | L-Ptc | | | |
| 86 | DL-Cys | DL-Ptc | | | |
| 87 | L-Abu | L-Ptc | | | |
| 88 | L-Abu | DL-Ptc | | | |
| 89 | DL-Abu | L-Ptc | | | |
| 90 | DL-Abu | DL-Ptc | | | |
| 91 | γAbu | L-Ptc | | | |
| 92 | γAbu | DL-Ptc | | | |
| 93 | DL-Phg (4Cl) | L-Ptc | | | |
| 94 | DL-Phg (4Cl) | DL-Ptc | | | |
| 95 | DL-Phg (2Cl 4CF$_3$) | L-Ptc | | | |
| 96 | DL-Phg (2Cl 4CF$_3$) | DL-Ptc | | | |
| 97 | DL-Phe (4Cl) | L-Ptc | | | |
| 98 | DL-Phe (4Cl) | DL-Ptc | | | |
| 99 | DL-Phe (4NO$_2$) | L-Ptc | | | |
| 100 | DL-Phe (4NO$_2$) | DL-Ptc | | | |
| 101 | DL-Val (αMe) | L-Ptc | | | |
| 102 | DL-Val (αMe) | DL-Ptc | | | |

*The individual amino acids are denoted by means of abbreviations which are generally customary in peptide chemistry (Houben-Weyl Volume 15/1, page 2 et seq.). Phosphinothricin is given the abbreviation "Ptc". The stereo-chemistry of the centers of asymmetry present is indicated in capital letters before the amino acid concerned.

B. EXAMPLES OF FORMULATIONS

1. A 20% strength aqueous solution is obtained from:
   20% by weight of active compound
   10% by weight of nonylphenol×10 EO
   20% by weight of ethylene glycol
   50% by weight of water 2. A wettable powder which is readily dispersible in water is obtained by mixing, and grinding in a pinned disk mill:
   25% by weight of active compound
   64% by weight of kaolin-containing quartz as inert material
   10% by weight of potassium ligninsulfonate and
   1% by weight of sodium oleylmethyltauride as wetting and dispersing agent.

C. BIOLOGICAL EXAMPLES

The damage caused to weed plants or the toleration by crop plants was rated by means of a code in which the activity is expressed by valuation numbers from 0 to 5. These have the following meanings:

0 = no effect or damage
1 = 0–20% effect or damage
2 = 20–40% effect or damage
3 = 40–60% effect or damage
4 = 60–80% effect or damage
5 = 80–100% effect or damage 1. Effect on Weeds by the Post-Emergence Technique Seeds or pieces of rhizome of monocotyledonous and dicotyledonous weeds were laid out in sandy loam soil in plastic pots (φ=9 cm), covered with soil and cultivated in a greenhouse under good conditions for growth. The test plants were treated in the three leaf stage three weeks after sowing.

The compounds according to the invention, formulated as wettable powders, as emulsion concentrates or as aqueous solutions, were sprayed onto the green parts of the plants at various dosages and at a water application rate equivalent to 600 l/hectare, and the effect of the preparations was rated visually in comparison with untreated controls after the test plants had stood for approx. 3–4 weeks in a greenhouse under optimum conditions for growth (temperature 23 plus/minus 1° C.; relative humidity 60–80%). The agents according to the invention display a good herbicidal activity in the post-emergence technique against a broad spectrum of grass-like weeds and weeds of economic importance.

TABLE 2

The herbicidal effect of the compounds according to the invention; post-emergence technique

| Product (Example No.) | Dosage (kg of a.i./hectare) | Herbicidal effect | | | | | |
|---|---|---|---|---|---|---|---|
| | | AVF | SAL | ECG | SIA | CRS | STM |
| 1 | 2.4 | 5 | 5 | 5 | 5 | 5 | 5 |
| | 0.6 | 4 | 4 | 5 | 5 | 5 | 4 |
| 2 | 2.4 | 5 | 5 | 5 | 5 | 5 | 5 |
| | 0.6 | 5 | 5 | 5 | 5 | 5 | 4 |
| 24 | 2.4 | — | — | 5 | 5 | 5 | 5 |
| | 0.6 | — | — | — | — | — | — |
| 72 | 2.4 | — | — | 5 | 5 | 5 | 5 |
| | 0.6 | — | — | — | — | — | — |
| 34 | 2.4 | 4 | 5 | 5 | 5 | 5 | 5 |
| | 0.6 | 3 | 4 | 5 | 5 | 5 | 4 |

Abbreviations:
AVF = *Avena fatua* (wild oats)
SAL = *Setaria lutescens* foxtail
ECG = *Echinochloa crus-galli* barnyardgrass
SIA = *Sinapis alba* (white mustard)
CFS = *Chrysanthemum segetum* corn marigold
STM = *Stellaria media* (starwort)
a.i. = active ingredient

We claim:
1. A compound of the formula I

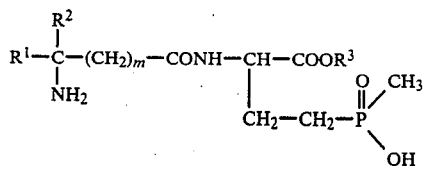

in which
- $R^1$ and $R^2$ independently of one another denote hydrogen, $(C_1-C_{12})$-alkyl, $(C_3-C_8)$-cycloalkyl, phenyl, benzyl or phenethyl, it being possible for the groups mentioned to be substituted in turn by halogen, $NH_2$, $OH$, $SH$, $NO_2$, $(C_1-C_4)$-alkoxy, $(C_1-C_4)$-alkylthio, $CF_3$, $(C_1-C_4)$-alkoxycarbonyl, $COOH$ or $CONH_2$, or
- $R^1$ and $R^2$ together denote an alkylene chain of 2–7 carbon atoms,
- $R^3$ denotes hydrogen or $(C_1-C_{12})$-alkyl and
- m denotes 0, 1, 2 or 3, and the salts thereof with bases and acids.

2. A compound of the formula I in which
- $R^1$ and $R^2$ independently of one another denote hydrogen, $(C_1-C_8)$-alkyl, phenyl, benzyl and phenylethyl, it being possible for the groups mentioned to be substituted in turn by $NH_2$, $OH$, $SH$, $(C_1-C_4)$-alkoxy, $(C_1-C_4)$-alkylthio, $(C_1-C_4)$-alkoxycarbonyl, $COOH$ or $CONH_2$, or
- $R^1$ and $R^2$, together with the carbon atom linking them, denote a cyclopentyl or cyclohexyl radical,
- $R^3$, denotes hydrogen or methyl and m denotes 0, 1 or 2, and the salts thereof.

3. A composition for controlling weeds, which contains an effective amount of the compound of the formula I as claimed in claim 1 in combination with an herbicidally acceptable carrier.

4. A process for controlling undesirable plant growth, which comprises applying an effective amount of a compound of the formula I as claimed in claim 1 to the plants to be controlled and/or to the area to be treated, using the pre-sowing, pre-emergence or post-emergence technique.

* * * * *